(12) United States Patent
Reiling

(10) Patent No.: US 7,516,018 B2
(45) Date of Patent: Apr. 7, 2009

(54) STRUCTURAL UNIT ANALYSIS

(75) Inventor: Stephan Reiling, Calison, NJ (US)

(73) Assignee: Tripos, L.P., St. Louis, MO (US)

( * ) Notice: Subject to any disclaimer, the term of this patent is extended or adjusted under 35 U.S.C. 154(b) by 0 days.

(21) Appl. No.: 10/206,387

(22) Filed: Jul. 25, 2002

(65) Prior Publication Data

US 2004/0024531 A1   Feb. 5, 2004

Related U.S. Application Data

(60) Provisional application No. 60/307,723, filed on Jul. 25, 2001.

(51) Int. Cl.
*G06F 19/00* (2006.01)
*C40B 30/02* (2006.01)

(52) U.S. Cl. .................. 702/27; 702/19; 506/8

(58) Field of Classification Search ............ 702/19, 702/22, 27, 127, 179
See application file for complete search history.

(56) References Cited

U.S. PATENT DOCUMENTS 5,025,388 A * 6/1991 Cramer et al. ............. 700/293

2001/0056329 A1 * 12/2001 Smellie et al. ............. 702/27

OTHER PUBLICATIONS

R. Agraval, H. Mannila, R. Srikant, H. Toivonen, and A. I. Verkamo. Fast discovery of association rules. In U. M. Fayyad, G. Piatetsky-Shapiro, P. Smyth, and R. Uthurusamy, editors, *Advances in Knowledge Discovery and Data Mining*, Knowledge Discovery in Databases, pp. 307-328. American Association for Artificial Intelligence, The MIT Press, 1996.

B. S. Everitt. *The Cambridge Dictionary of Statistics*. Cambridge University Press, 1998.

P. Sprent and N. C. Smeeton. *Applied Nonparametric Statistical Methods*. Texts in Statistical Science. Chapman & Hall/CRC, London, 3rd edition, 2000.

* cited by examiner

*Primary Examiner*—Lori A Clow
(74) *Attorney, Agent, or Firm*—Laurence Weinberger

(57) ABSTRACT

A computer implemented method is disclosed for analyzing a large data set of chemical compounds for which there is a measured activity in the same assay for each compound to determine the structural units which are responsible for the observed activity of the compounds.

4 Claims, 4 Drawing Sheets

Description of process

Flowchart

STRUCTURAL UNIT ANALYSIS

The benefit of U.S. Provisional Patent Application No. 60/307,723 filed Jul. 25, 2001 is hereby claimed.

FIELD OF THE INVENTION

This invention relates to a method for identifying from a series of molecules for which an activity in an assay has been determined those molecular substructures which are responsible for the observed activity.

BACKGROUND OF THE INVENTION

In many areas of chemical research, especially pharmaceutical research, a large number of chemical compounds may be identified which exhibit chemical or biological activity in the same assay. In drug research these compounds are identified through various means including the technique of high throughput screening which has seen wide implementation in recent years. In order to understand the basis for the observed activities in order to enable the design of chemical compounds with higher activity, an understanding of the chemical substructures which are responsible for the observed activities is desirable.

MOLECULAR MODELING ENVIRONMENT

Generally, all calculations and analyses to practice the method of the present invention are implemented in a modern computational chemistry environment using software designed to handle molecular structures and associated properties and operations. For purposes of this Application, such an environment is specifically referenced. In particular, the computational environment and capabilities of the SYBYL and UNITY software programs developed and marketed by Tripos, Inc. (St. Louis, Mo.) are specifically utilized. Software with similar functionalities to SYBYL and UNITY are available from other sources, both commercial and non-commercial, well known to those in the art. A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a Silicon Graphics, Inc. Challenge-M computer having a single 150 Mhz R4400 processor with 128 Mb memory and 4 Gb hard disk storage space.

DETAILED DESCRIPTION OF THE INVENTION

Structural Unit Analysis (SUA) is a technique to identify relevant structural series in chemical data. A "structural series" is here defined as "a set of molecules having certain structural feature in common", and "relevant" means simply that not all possible structural series in the data are identified, but only those that are significant for explaining the observed activity. SUA at this point is not intended to be used for predicting the activity of unknown compounds. Its goal is only the identification of structural patterns in large data sets, these structural patterns can then be used in other predictive methods. However, it might be possible to extend SUA to be predictive (see future development).

SUA is not clustering. Typical clustering uses a similarity measure, and then clusters the compounds to maximize the similarity within clusters and minimizes the similarity between clusters. Most of these similarity measures look at the whole structure and compute the similarity between structures using all of the structural features of a compound. By contrast, SUA looks only at a limited number of features of a compound at the same time. Similar to fuzzy clustering approaches, in SUA a compound can belong to more than one series.

Initial Implementation of the Invention

Figure 1:
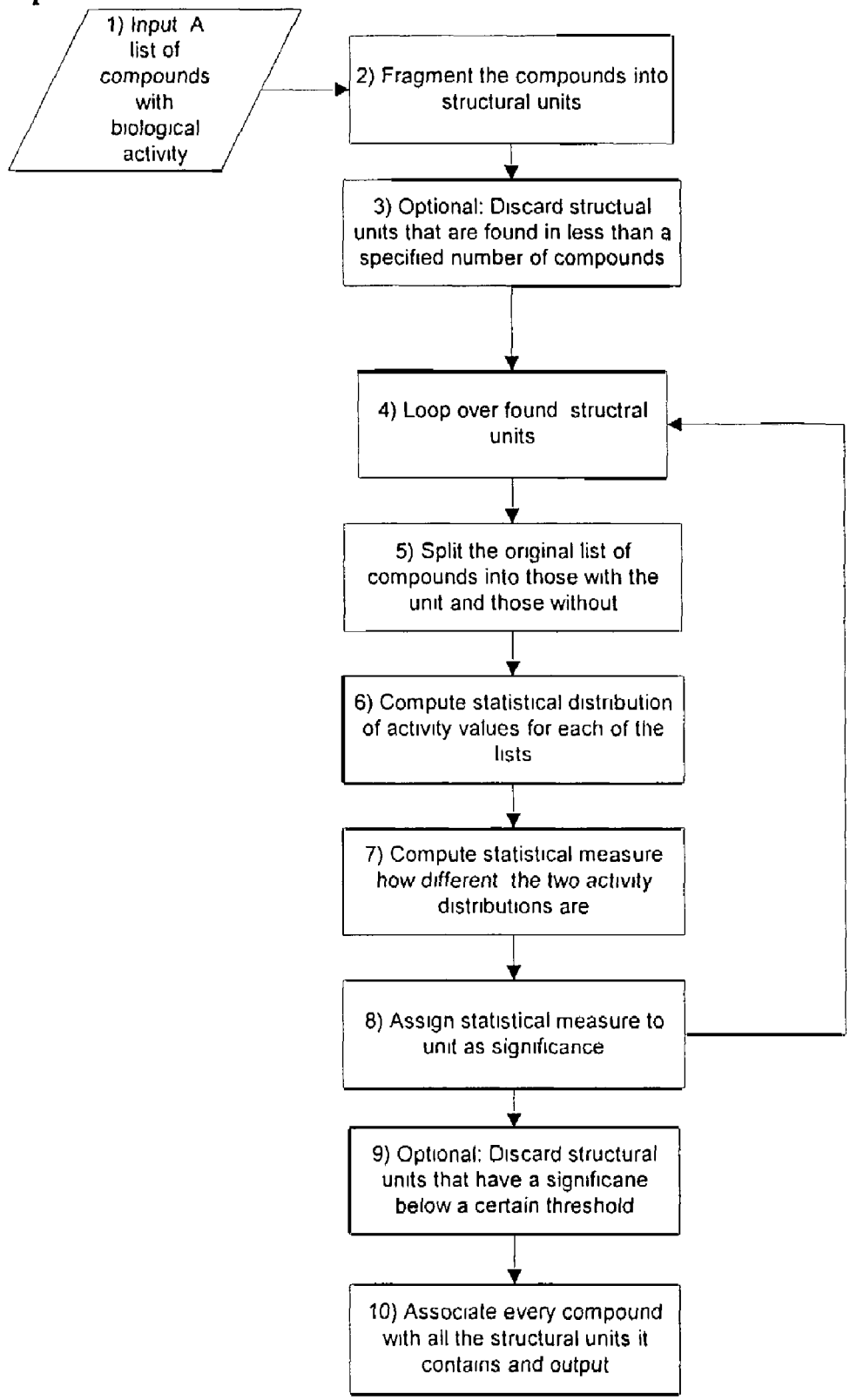
FIG. 1 shows a schematic outline of the method of the invention to compute the significance for single structural units.

To start the analysis, information on the molecules' activity in one or more biological assays is needed. The method of this invention was initially implemented as shown schematically in FIG. 1. These steps compute the significance for single structural units. The identified steps perform the following functions.

Step 1. The list of compounds can contain one measured activity per compound or several different ones (different biological assays).

Step 2. Fragmentation splits the compounds in an intelligent way by first splitting all rotatable bonds, then reconstructing some of the rotatable parts as long as they are not connected to a rigid part. The result is the compound split into rigid and flexible units.

Step 3. An optional step discards the units that occur in less than a specified number of compounds.

Step 4. Starts to loop over all found structural units.

Step 5. Take the list of activities and create two lists of activities from it: One list containing the activities of the compounds with the current structural units and one list of the compounds without it.

Step 6. For the two lists created in step 5, compute for each of the two lists the statistical distribution of the numerical values of the activity.

Step 7. Perform a statistical test, for example an analysis of variance (ANOVA), that computes how much the two activity distributions differ. This gives a measure of the significance of the structural unit for the observed activity. Other tests than ANOVA are possible (Shannon Entropy, for example) as will be discussed below.

Step 8. Store the computed significance for each structural unit (end of loop, return to step 4).

Step 9. Optional: Discard all units with a significance below a certain value.

Step 10. Assign each compound to all the units left from the previous steps that it contains and output the resulting clusters.

Those skilled in the art will understand that the resulting clusters associate different structural features with the observed activity.

Figure 2:
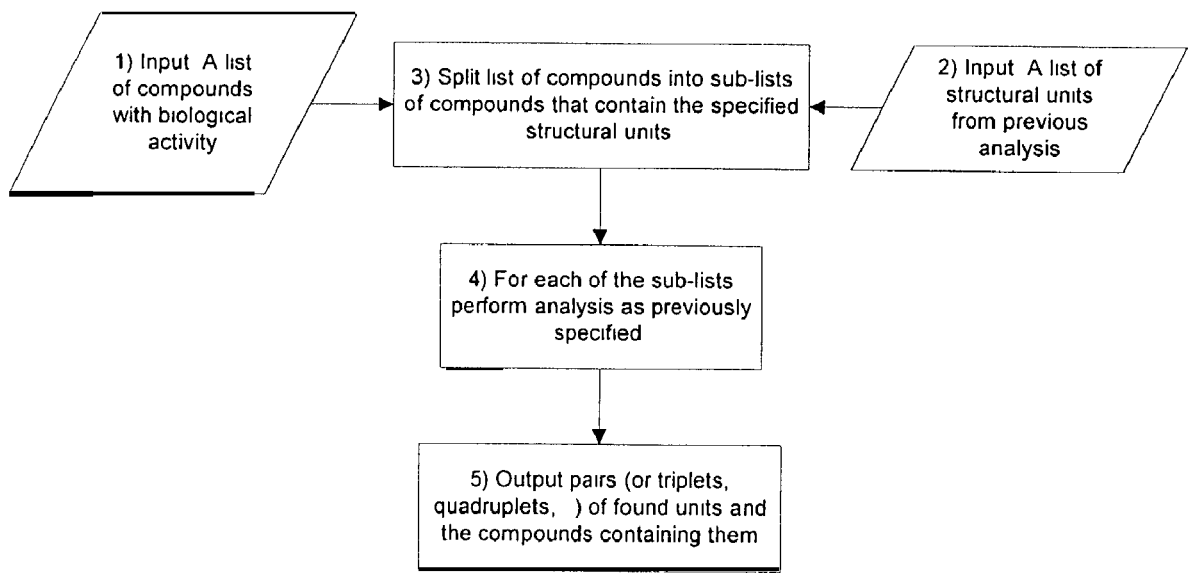
FIG. 2 shows a schematic outline of the method of the invention implemented for larger units.

As noted, these steps above compute the significance for single structural units. Based on this first pass, the method can be used to look recursively at pairs, triplets, etc. of structural units. FIG. 2 shows schematically the application to larger units. The steps identified in FIG. 2 perform the following functions.

Step 1. Same as in previous flowchart of FIG. 1.
Step 2. This is the result of the previous flow (or the result of the current flow). The method can work recursively.
Step 3. For each of the structural units given as Input 2, extract from the list given as Input 1 the compounds containing this unit.
Step 4. For each of the sub-lists generated in step 3) perform analysis depicted in previous flow.
Step 5. Output pairs (or triplets, quadruplets, etc . . . depending on Input 2).

Again, those skilled in the art will understand that the resulting clusters associate different structural units (now comprised of more than just a single unit) with the observed activity.

Figure 4:
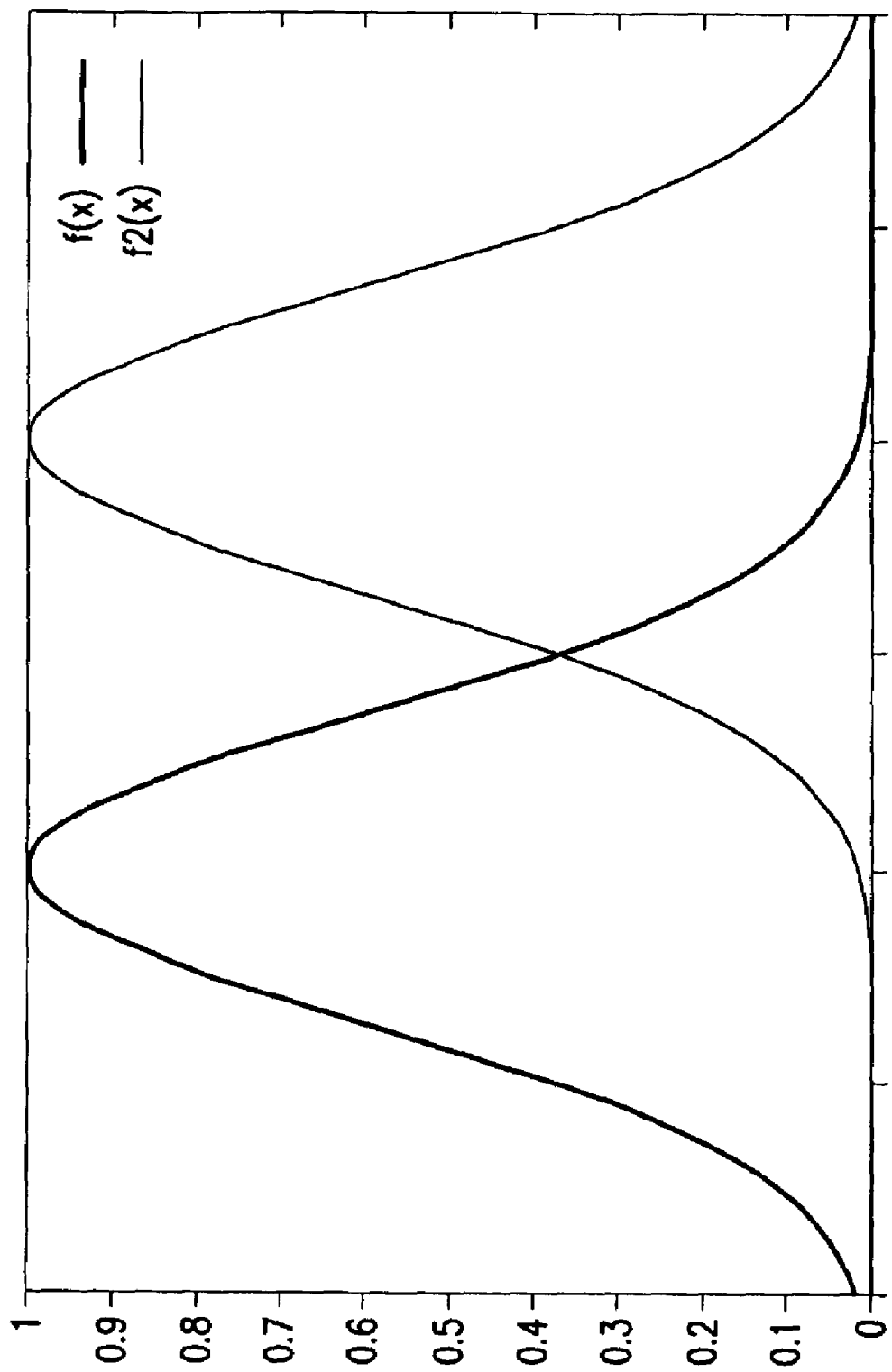
FIG. 4 shows the two idealized distributions of activity that result from splitting the list of activities.

In steps 5, 6, and 7 the list of activities is split into two lists, one list containing the activities of compounds that have the structural unit currently under consideration and the other one containing the activities of the compounds that do not have this unit. This process will give two distributions of activity, in idealized form something like that shown in FIG. 4.

An analysis of variance (ANOVA) gives an F-value indicating how much the distribution of activities between the two lists is statistically different (note: ANOVA assumes a standard distribution of the observable). As will be discussed below, there is no reason to believe that the data set would generate a normal distribution and other tests need to be considered. The F-value is always positive. If the mean activity of the compounds with the structural unit is "better" than the other list the F-value gets a positive sign, if its worse it gets a negative sign. This process basically determines for every structural unit how significantly it contributes to the observed activity. It is also useful during the process to eliminate units that appear in fewer than a few compounds (typically 3). This still shows chemical series and removes a lot of noise. Every compound gets assigned to all the structural units that are found in it and the result is written out as clusters.

DESCRIPTION OF PREFERRED EMBODIMENT

Figure 3:
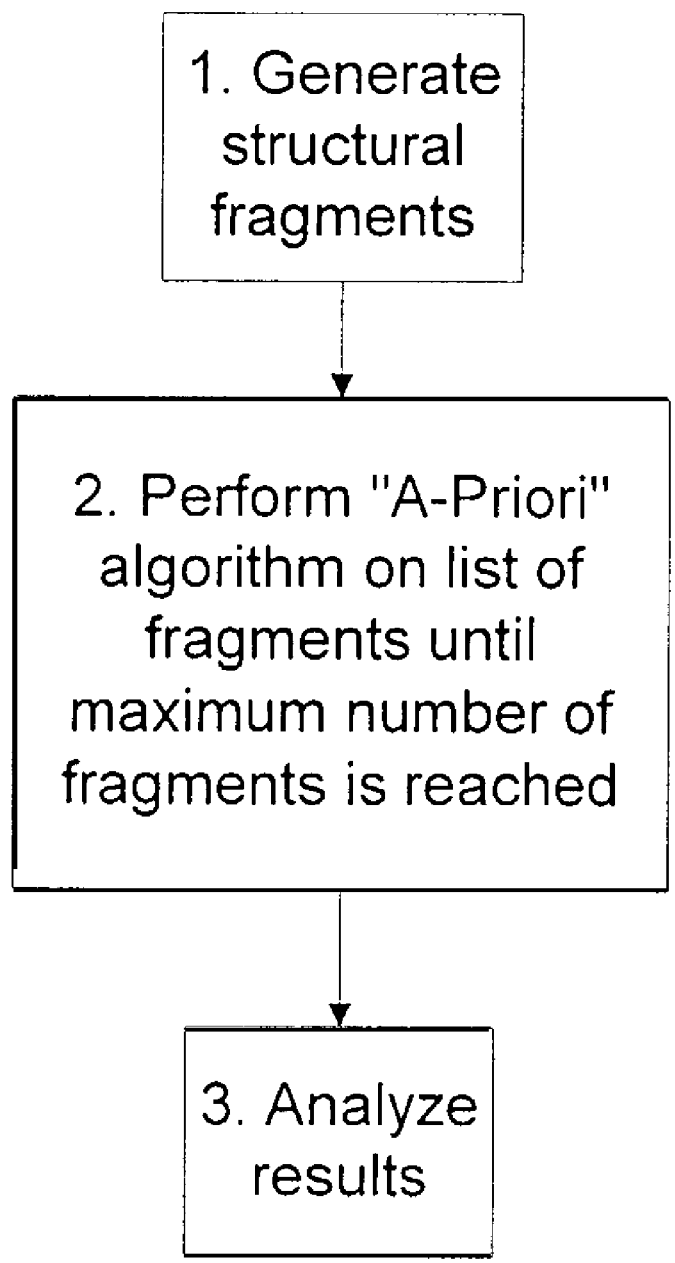
FIG. 3 shows a schematic of the invention in its most general form.

In its most general form, the method of the present invention consists of essentially three steps as depicted in the attached flow chart of FIG. 3. The three steps are described below:

1. Generation of Structural Fragments

Fragment the molecular structures into "units". The size of the fragments can range from a single atom to whole molecules, if these molecules can not be fragmented. The method does not fragment a compound into smaller fragments in such a way as Unity fingerprints for example does this, but it cuts the compounds into bigger connected "units" (hence the name). The way the fragments are generated is not important for the method, the fragmentation can be rule based as taught in the initial methodology above or work with predefined fragments. These units are roughly defined by the boundary in the molecule where rotatable and non-rotatable pieces of the structure are connected. The result of this first step is a list of all fragments found in the set of molecules to be analyzed that should be used for the next step.

2. Generating Combinations of Fragments

In this step the list of structural fragments generated in step 1 are combined using modifications of the "A-Priori" algorithm which was originally developed for association rule mining. In the preferred method, two ways of combining fragments are taught (described below), both utilizing a modified version of the "A-priori" algorithm. The algorithm is iterative, in each iteration fragments from the list are combined with each other. After every iteration, a new list of bigger fragments is generated from the list of the previous iteration. The user can choose to terminate the algorithm once fragments of a specified size are generated or let the algorithm run to completion. These combinations of units (or structural features, in a 2D sense), define a structural series. When all these combinations of units are created, a lot of possible structural series (typically more then there are structures in the data set) are generated. We are not interested in all of these possible series, only in the ones relevant for the observed activity.

For every combination of fragments, the algorithm checks in how many molecules this combination is found and based on this information determines if this combination of fragments should be merged with more fragments in subsequent iterations. The result of this step is a list of combinations of fragments that were found in the structures to analyze.

3. Analysis of Generated Hypothesis

The last step takes the list of combinations generated in the previous step and analyses it. This analysis can be computational (statistical analysis, for example) or visual (graphing and inspection by the user). The combinations of units generated by the A-priori algorithm have to be seen as possible series that are found in the data set. These proposals still need to be evaluated on their relevance for the observed activity. For this a statistical significance test similar to the ANalysis Of VAriance (ANOVA) is used. Basically, the combinations of units are treated as a factor influencing the observed activity. ANOVA computes a probability that the combination of units under consideration is significant or just caused by random chance.

Because, as noted above, the data sets under investigation are usually highly skewed to the left (lots of inactive compounds, only few active compounds), the usual parametric ANOVA, which assumes a Gaussian distribution, is not used but rather the Kruskal-Wallis test which makes no assumptions about the form of the distribution of the data. As will be described below, this is combined with simple Bayesian reasoning.

Detailed Description of Each Step:

Fragmenting the Structures

The fragmentation of structures into units is straightforward and is governed by the following rules. "Rotatable bond" here refers to the Unity definition of a rotatable bond. 1. If a rotatable bond is attached to an atom to which non-rotatable bonds are attached, cut this bond.

2. Cut the bond of a halogen atom attached to a ring (which is not a rotatable bond per se).

3. Hydrogens attached to a carbon are removed.

The cutting of these bonds segments the molecule in such a way that all non-rotatable parts of the molecule are separated from the rotatable parts of the molecule. The bonds within the non-rotatable or rotatable parts are kept intact. There is no notion of the size of these parts (or units). The units can be in size anywhere from 2 atoms (e.g. N—H, CN) or tens of atoms for fused ring systems. The underlying concept is that the rotatable parts of the molecule are only there to provide internal degrees of freedom to position the rigid or interacting parts of the molecule within the receptor site.

Generating Combinations of Units

As mentioned before, a modified version of the A-priori[1] approach is used to efficiently generate combinations of units.

The following briefly describes the A-priori algorithm, and the modifications that were made for SUA.

The Apriori Algorithm

The Apriori algorithm was developed to find associations in data sets, for example in sales records. Association are of the form A←{B, C, D} which means that the presence of B,C,D together implies that A is also present. There are two attributes for an association: the support and the confidence. The support is the number of occurrences the association was observed, the support is the proportion of all occurrences of {B,C,D} in which A was also observed. Using an example from sales records, an association might state: "If a customer bought coffee and cereals, in 99% of the cases the customer also bought milk, which was observed 15000 times." The Apriori algorithm was developed to find associations rules in large data sets. The algorithm takes as parameters the minimum support and confidence, and the maximum number of feature to combine. The algorithm is iterative. It starts with a set of all features {A,B,C,D,E}, this is called the frontier set. It then combines the items in the frontier set with each other. This would create a new feature set {(A-B),(A-C),(A-D), ... ,(D-E)}, but it will eliminate combinations for which the support is below the given threshold, so that certain combinations are nor created. The resulting combinations (say {(A-B),(B-D),(C-E), ... }) become the new frontier set and the algorithm starts over, until the specified search depth is reached. For SUA, the algorithm was modified in the following ways:

1. Instead of computing the confidence, a statistical significance is computed (described below). After each iteration of the A-priori algorithm, the entries of the new frontier list are checked for their statistical significance. The entries that are above the specified significance threshold are stored for later output. The default behavior of the algorithm is also to remove the significant entries from the frontier. The reason is that these significant entries will generate a large number of significant entries that do not contribute any new information. If the entry (A-A) is significant, most of the combinations that are generated from this entry will also be significant. After every iteration a statistical test correction, a Simes-modified Bonferroni correction[2], is performed. If this correction judges a previously identified combination of units as likely being caused by random chance, since now more combinations are available, the affected combination is added into the frontier again to generate more combinations that could be significant. Apart from the statistical test, an additional Bayesian analysis[3] is performed to asses if a certain series is "good". For this analysis, the molecules in a series and the units that define the series are used. As more evidence becomes available as the algorithm progresses, which series are selected by the Bayesian analysis will change.
2. Since combinations of non-significant items can be significant, an initial fixed pool of features is used. This means that beginning with a feature set of {A,B,C,D,E}, after generating the next frontier set this frontier set (say {(A-B),(B-D),(C-E), ... }) would not be combined with itself, but with the original feature set {A,B,C,D,E} again.
3. Introduction of structural constraints. The goal of SUA is to create significant structural series. So far only the presence or absence of a structural unit was considered, which does not result in "good" structural series. To put more emphasis on structural consistency, structural constraints were added to the algorithm. Instead of just looking at the presence or absence of structural units, pairs of structural units are taken as features. This approach is similar to atom pair fingerprints. A binary fingerprint is created for each molecule, in which every bit indicates the presence or absence of a certain pair of units, at a given distance. Here, the distance is expressed as bonds. As an example, bit number 28 might indicate that the molecule contains a phenyl ring two bonds away from a carboxyl group. To improve performance, units consisting only of single-bonded carbons or hydrogens attached to these carbons (aliphatic side chains) are discarded. This information is contained in the distances between the units. This is still not sufficient. When bits are combined by the apriori algorithm, still only the presence or absence of bits (i.e. pairs of structural units) is considered. As an example, when bits 256 and 128 are combined, this only means that the molecule has "a Hydroxyl two bonds away from a phenyl", and somewhere else in the molecule "an Amino group three bonds away from a carboxyl". This does not necessarily define a structural series, and might result in structural inconsistent molecules in the same series. An improvement is to require that the two pairs to combine share a common unit. This would not allow the combination given above, since the two pairs do not share a common unit. The combination "a Hydroxyl two bonds away from a phenyl" combined with "a sulfoxide one bond away from a phenyl" would fulfill this constraint, but this only means that somewhere in the molecule these two pairs of units have to be present. This still results in inconsistent structural series. The approach taken in the method of the present invention is to require that the two pairs to combine not only share a unit, but also that the atoms of the shared unit are the same. As an example, a frontier entry like (A-B) can be combined with entry (B-C), resulting in (A-B-C), but it can not be combined with (C-D), since the two entries do not share a common unit. With entries of two or more pairs (three or more units), branching is possible. An entry like (A-B-B) when combined with the entry (B-D) can result in the two entries (A-B-B-D) and (A-B(-B)(-D)). These two possibilities have identical bit patterns in the binary unit pair fingerprint.

Determination of Relevance—Statistical Significance Test

The most common statistical significance test to decide if a parameter plays a factor for an observed variable is the ANalysis Of VAriance (ANOVA). This is a parametric test, based on the assumption that random samples from a population with a distribution of the normal form (Gaussian). For biological activity, this almost never the case. Here the distribution shows typically a large number of inactive (or less active) compounds and only a relatively small number of active compounds. The actual form of the distribution is not known, and it might change from one data set to another. For these reasons a non-parametric significance test that makes no assumptions about the underlying distribution was chosen. The significance test used here is the Kruskal-Wallis test corrected for the occurrence of ties[4]. The test is based on the ranks of the data, and as a first step the data items are sorted (ranked). Especially in HTS data, where the activity is sometimes reported only as an integer, ties in the ranking can occur. The general accepted practice is then to replace all tied ranks with the average rank the ties would have had, if the tie had not occurred. For example, in the data set 1,1,2,3,3,3,4 the following ranks would be assigned: {1.5, 1.5, 3, 5, 5, 5, 7}. The Kruskal-Wallis test corrected for ties is defined as follows:

$$T = \frac{(N-1)S_k - C}{S_r - C} \text{ with} \quad (1)$$

$$C = \frac{N(N+1)^2}{4} \quad (2)$$

$$S_r = \sum_{i,j} r_{ij}^2 \quad (3)$$

$$S_k = \sum_i \frac{\left(\sum_j r_{ij}\right)^2}{n_i} \quad (4)$$

where N is the number of all observations, k is the number of samples, i-th sample consisting of $n_i$ observations, and the j-th of these being $x_{ij}$. For N moderate or large (typically $N \geq 5$), T follows a $X^2$-distribution with k−1 degress of freedom, which allows to compute the probability that the effect of the parameter is caused by random chance. This is more descriptive and allows to compare significance values across different tests.

EXAMPLE

NCI-H23 Cancer Data

To illustrate the method of the invention, a public data set from the *Discovery of Therapeutics Program* (DTP) of the National Cancer Institute (NCI) was used. The NCI has screened a large number of compounds against a variety of cancer cell lines and made the results available to the public. For the example here, the NCI-H23 cell line (nonsmall cell lung cancer) was chosen. The data set consists of 35000 compounds. The activity used here is the negative logarithm of 50% growth inhibition concentration (pGI50), from the August 2000 version of the data set. The data set shows an activity range from −5 to 12. An activity threshold of pGI50$\geq$6 was used for this study, resulting in 1848 actives. Table 1 summarizes the parameters used.

TABLE 1

Parameters used for NCI-H23 example

| Parameter Name | Value |
|---|---|
| Maximum number of bonds | 2 |
| Search Depths (number of pairs) | 3 |
| P-value | 0.05 |
| Minimum Support | 7 |

Using a maximum bond distance of 2 emphasizes the creation of series that share scaffold-like features. Increasing the bond parameter will create more pharmacophore-like feature sets. In practice a maximum search depth of 3 has shown to be sufficient.

Further Extensions of the Method

As will be readily apparent to those skilled in the art, the information derived from the practice of the present invention enables a number of additional methods to further examine the structure-activity relationships (SARs) inherent in similar large data sets. Some of these are set forth below:

a. Storing the found rules (which combinations of units increase activity, which decrease it) in a database for several assays separately permits data mining on this rule set. (For instance: show all the rules that are identical across the assays; or show the rules that differentiate between the assays).

b. Performing hierarchical clustering on the structural units to allow the user easy navigation through the resulting tree.

c. Using the identified units as input into a combinatorial docking experiment.

d. Automating the recursive invocation of this process (going from single units to pairs, triplets, etc) by using methods like recursive partitioning or a-priori association rule mining).

e. Performing the above analysis until a common core and the variable structural units are identified, then performing a COMFA analysis where the common core is aligned.

REFERENCES CITED

1. R. Agraval, H. Mannila, R. Srikant, H. Toivonen, and A. I. Verkamo. Fast discovery of association rules. In U. M. Fayyad, G. Piatetsky-Shapiro, P. Smyth, and R. Uthurusamy, editors, *Advances in Knowledge Discovery and Data Mining*, Knowledge Discovery in Databases, pages 307-328. American Association for Artificial Intelligence, The MIT Press, 1996.
2. B. S. Everitt. *The Cambridge Dictionary of Statistics*. Cambridge University Press, 1998.
3. Gelman and Others. *Bayesian Data Analysis*. Texts in Statistical Science. Chapman & Hall/CRC, London.
4. P. Sprent and N. C. Smeeton. *Applied Nonparametric Statistical Methods*. Texts in Statistical Science. Chapman & Hall/CRC, London, 3rd edition, 2000.

I claim:

1. A computer assisted method for determining the molecular structural units found in small molecules, for which a measured activity in the same assay has previously been determined for each molecule, that are responsible for the observed activities of the molecules comprising the following steps all of which are performed on a computer:
    a) fragmenting the molecules into structural units;
    b) determining all combinations of the structural units which may be formed from the individual units;
    c) associating the activities of the molecules from which the combinations are derived with each structural unit and each combination;
    d) selecting a single structural unit or combination of structural units for analysis:
    e) creating two lists, a first list containing the activities of compounds containing the selected structural unit, and a second list containing the activities of compounds that do not have the selected structural unit;
    f) performing a statistical analysis on the activity distributions of the two lists to determine whether the association of the structural unit or combination of structural units is relevant to the measured activity;
    g) assigning every molecule to all the structural units found in the molecule which were determined to be relevant in step f); and
    h) outputting the structural units relevant to the measured activities in association with the activities and the molecules containing the structural units, wherein the associated molecules form clusters associating different structural features with observed activity.

2. The method of claim 1, step (a) in which the molecules are fragmented into rigid and flexible units.

3. A computer assisted method for determining the molecular structural units found in small molecules, for which a measured activity in the same assay has previously been determined for each molecule, that are responsible for the observed activities of the molecules comprising the following steps all of which are performed on a computer:

a) fragmenting the molecules into structural units;
b) determining all combinations of the structural units which may be formed from the individual units;
c) associating the activities of the molecules from which the combinations are derived with each structural unit and each combination;
d) selecting a single structural unit or combination of structural units for analysis:
e) creating two lists, a first list containing the activities of compounds containing the selected structural unit, and a second list containing the activities of compounds that do not have the selected structural unit;
f) performing a statistical analysis on the activity distributions of the two lists to determine whether the association of the structural unit or combination of structural units is relevant to the measured activity; and
g) storing the results of the testing for each unit or combination of structural units;
h) repeating steps d) through g) until all structural units and combinations of structural units have been tested;
i) assigning every molecule to all the structural units found in the molecule which were determined to be relevant in step f); and
j) outputting the structural units relevant to the measured activities in association with the activities and the molecules containing the structural units, wherein the associated molecules form clusters associating different structural features with observed activity.

4. The method of claim 3, step (a) in which the molecules are fragmented into rigid and flexible units.

* * * * *